US007621926B2

(12) United States Patent
Wixey et al.

(10) Patent No.: US 7,621,926 B2
(45) Date of Patent: Nov. 24, 2009

(54) MULTI-FIRE SURGICAL CLIP APPLIER

(75) Inventors: Matthew A. Wixey, Dana Point, CA (US); Thomas D. Wachli, Aliso Viejo, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 259 days.

(21) Appl. No.: 10/962,093

(22) Filed: Oct. 7, 2004

(65) Prior Publication Data

US 2005/0234478 A1    Oct. 20, 2005

Related U.S. Application Data

(60) Provisional application No. 60/562,940, filed on Apr. 16, 2004.

(51) Int. Cl.
*A61B 17/10* (2006.01)
(52) U.S. Cl. .................................. 606/142; 606/139
(58) Field of Classification Search ......... 606/139–142, 606/143; 227/175.1, 182.1
See application file for complete search history.

(56) References Cited

U.S. PATENT DOCUMENTS

| 2,778,925 A * | 1/1957 | Gross et al. ............... 219/69.15 |
| 4,425,915 A | 1/1984 | Ivanov |
| 4,448,193 A | 5/1984 | Juanov et al. |
| 4,449,530 A | 5/1984 | Bendel et al. |
| 4,478,220 A | 10/1984 | Di Giovanni et al. |
| 4,491,133 A | 1/1985 | Menges et al. |
| 4,522,207 A | 6/1985 | Klieman et al. |
| 4,576,166 A | 3/1986 | Montgomery et al. |
| 4,799,481 A | 1/1989 | Transue et al. |
| 4,850,355 A | 7/1989 | Brooks et al. |
| 4,979,950 A | 12/1990 | Transue et al. |

(Continued)

FOREIGN PATENT DOCUMENTS

DE    296 01 815 U1    3/1996

(Continued)

OTHER PUBLICATIONS

International Search Authority, International Search Report and Written Opinion for International Application PCT/US2005/011836, mailed Jan. 31, 2006.

(Continued)

*Primary Examiner*—(Jackie) Tan-Uyen T Ho
*Assistant Examiner*—Jing Ou
(74) *Attorney, Agent, or Firm*—John F. Heal; Patrick Y. Ikehara

(57) ABSTRACT

Clip appliers to apply a surgical clip and methods concerning the same are provided. One provided applier has a cartridge and an actuator. The rack mechanism causes a feeder to move proximally as a closure member moves distally, such that jaw members move together to crimp a clip there between. The rack mechanism also causes the feeder to move distally as the closure member moves proximally, such that a crimped clip is released and another clip is fed into the jaw members. The rack mechanism further includes a rack connected to the closure member in which the closure member and the rack are arranged to move synchronously throughout the releasing of a crimped clip and feeding of another clip, e.g., an opening stroke.

26 Claims, 16 Drawing Sheets

U.S. PATENT DOCUMENTS

| | | | |
|---|---|---|---|
| 5,049,152 A | 9/1991 | Simon et al. | |
| 5,084,057 A | 1/1992 | Green et al. | |
| 5,100,420 A | 3/1992 | Green et al. | |
| 5,171,247 A | 12/1992 | Hughett et al. | |
| 5,171,249 A | 12/1992 | Stefanchik et al. | |
| 5,197,970 A | 3/1993 | Green et al. | |
| 5,207,692 A | 5/1993 | Kraus et al. | |
| 5,336,229 A | 8/1994 | Noda et al. | |
| 5,366,134 A | 11/1994 | Green et al. | |
| 5,382,254 A | 1/1995 | McGarry et al. | |
| 5,382,255 A | 1/1995 | Castro et al. | |
| 5,403,327 A | 4/1995 | Thorton et al. | |
| 5,423,835 A | 6/1995 | Green et al. | |
| 5,445,167 A | 8/1995 | Yoon et al. | |
| 5,462,558 A | 10/1995 | Kolesa et al. | |
| 5,474,567 A | 12/1995 | Stefanchik et al. | |
| 5,483,952 A | 1/1996 | Aranyi et al. | |
| 5,509,920 A | 4/1996 | Phillips et al. | |
| 5,527,318 A | 6/1996 | McGarry | |
| 5,527,320 A | 6/1996 | Carruthers et al. | |
| 5,582,615 A | 12/1996 | Foshee et al. | |
| 5,601,573 A | 2/1997 | Fogelberg et al. | |
| 5,601,574 A | 2/1997 | Stefanchik et al. | |
| 5,607,436 A | 3/1997 | Pratt et al. | |
| 5,626,592 A | 5/1997 | Phillips et al. | |
| RE35,525 E | 6/1997 | Stefanchik et al. | |
| 5,634,930 A * | 6/1997 | Thornton et al. | 606/143 |
| 5,645,551 A | 7/1997 | Green et al. | |
| 5,645,553 A | 7/1997 | Kolesa et al. | |
| 5,681,330 A | 10/1997 | Hughett et al. | |
| 5,700,270 A | 12/1997 | Peyser et al. | |
| 5,700,271 A * | 12/1997 | Whitfield et al. | 606/143 |
| 5,833,696 A * | 11/1998 | Whitfield et al. | 606/143 |
| 5,833,700 A | 11/1998 | Fogelberg et al. | |
| 5,904,693 A * | 5/1999 | Dicesare et al. | 606/143 |
| 5,938,667 A | 8/1999 | Peyser et al. | |
| 6,099,537 A * | 8/2000 | Sugai et al. | 606/143 |
| 6,139,555 A | 10/2000 | Hart et al. | |
| 6,258,105 B1 | 7/2001 | Hart et al. | |
| 6,423,079 B1 | 7/2002 | Blake, III | |
| 6,695,854 B1 | 2/2004 | Kayan et al. | |
| 6,966,919 B2 * | 11/2005 | Sixto et al. | 606/153 |
| 2002/0045909 A1 | 4/2002 | Kimura et al. | |
| 2003/0047582 A1 | 3/2003 | Sonnenschein et al. | |

FOREIGN PATENT DOCUMENTS

| | | |
|---|---|---|
| EP | 0 834 286 A | 4/1998 |
| EP | 0 286 921 A | 10/1998 |

OTHER PUBLICATIONS

European Search Authority, Partial International Search Report for International Application No. PCT/US2005/011836, mailed Oct. 21, 2005.

* cited by examiner

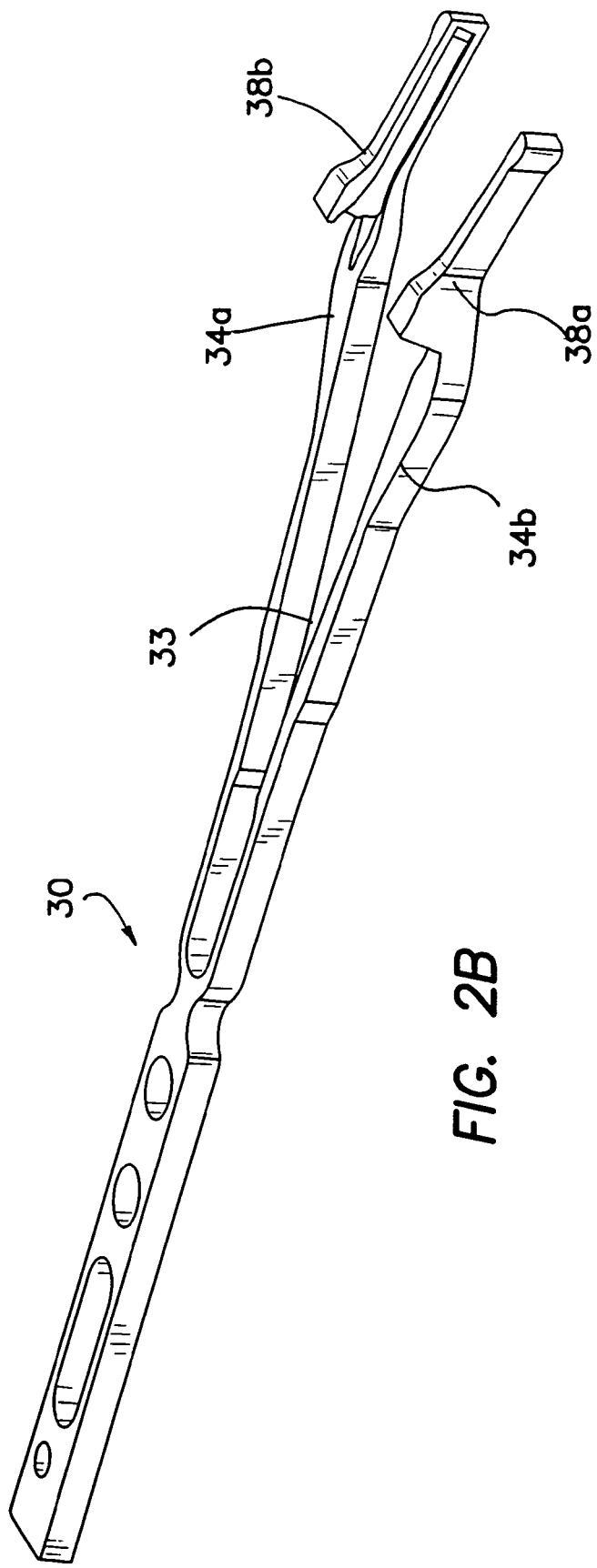

MULTI-FIRE SURGICAL CLIP APPLIER

CROSS-REFERENCE TO RELATED APPLICATIONS

This application claims the benefit of U.S. Provisional Application No. 60/562,940, filed Apr. 16, 2004, the disclosure of which is hereby incorporated by reference as if set forth in full herein.

BACKGROUND

The present invention relates generally to surgical instruments and, more to particularly, to fully controllable multi-fire clip appliers.

Clip appliers are frequently used in endoscopic, laparoscopic and other surgeries related to the use of a trocar or a small entry incision for the application of hemostatic clips. Typically, a clip is placed between the jaw of a clip applier to be crimped onto a vessel, tissue or an object, such as another clip. Some clip appliers have difficulty in placing the clips reliably and properly between the jaw to promote crimping and avoid clips from jamming before reaching the jaw. Clip appliers having the characteristics of simplicity in construction, reliability in operation and sufficiently economical to allow reusability or disposability are also hard to achieve. Complicated mechanical components or assemblies of a clip applier can also be expensive to produce, complex to manufacture and difficult to sterilize.

Additionally, rapidly applying multiple successive clips, which is often common, especially when a surgeon needs to curtail the loss of blood from a bleeding vessel, can prove to be a challenge. The timing or time period for placing the clip between the jaw of the clip applier after the jaw is sufficiently open to properly receive the clip and yet before a user attempts to crimp the clip is often limited. Providing the clip before the jaw is sufficiently open to receive the clip can cause the clip to jam within the applier or not be properly seated between the jaw and thereby ultimately causing the clip or tissue to be improperly crimped or unintentionally released from the jaw.

Furthermore, with some clip appliers, to permit rapid application of multiple clips, if a force is used to swiftly place the clip into the jaw, such a force may eject the clip from the jaw or improperly place or misalign the clip between the jaw. Also, if the jaw is not sufficiently opened, the clip may be deformed as the clip is forced into the jaw.

As such, ensuring that clips are fed in a manner that promotes crimping and substantially eliminates jamming is desirable. Tactile feedback provided to the surgeon or user and instrument operation should also be natural and comfortable thereby avoiding undue, obtrusive or wasted motions or force applied to or by the instrument.

SUMMARY

In one aspect of the present invention, a clip applier is provided to ensure that the jaw is sufficiently open prior to moving a clip into the jaw. The clip applier in one embodiment of the present invention ensures the timing of opening the jaw corresponds to moving a clip into the jaw. Components, assemblies or mechanisms used to accomplish this are simplified to reduce costs and difficulties in manufacturing, assembly, reliability and sterilization. In one aspect of the present invention, mechanisms to open the jaw interact with mechanisms to move a clip into the jaw to provide simultaneous movement of these mechanisms throughout operation of the clip applier and/or no additional force or components are used on racks associated with these mechanisms.

A clip applier applying a surgical clip, in one aspect of the present invention, comprises a cartridge with a proximal end and a distal end and an actuator. The cartridge includes a feeder having a proximal end and a distal end, a rack mechanism, a closure member having a proximal end and a distal end, and a pair of opposing crimping members extending outwardly from the distal end of the closure member. The rack mechanism has a spur gear, a first rack connected to the feeder, and a second rack connected to the closure member. The actuator coupled to the proximal end of the cartridge and the proximal end of the closure member. The actuator is arranged to open the opposing crimping members during an opening stroke. The closure member and the second rack are arranged to move synchronously throughout the opening stroke.

In another aspect of the present invention, a clip applier applying a surgical clip comprises a cartridge and a closure member. The cartridge with a proximal end and a distal end includes a feeder having a proximal end and a distal end, a closure member having a proximal end and a distal end, a pair of opposing crimping members extending outwardly from the distal end of the closure member, and a rack mechanism. The rack mechanism has a spur gear, a first rack connected to the feeder, and a second rack directly connected to the closure member. The closure member and the second rack are only movable together. The actuator is coupled to the proximal end of the cartridge and the proximal end of the closure member.

In yet another aspect of the present invention, a method of applying a surgical clip having crimping members coupled to a closure member coupled to a feeder is provided. The method provides extending a feeder of a clip applier to move a clip into crimping members of a clip applier, extending a closure member of the clip applier to close the crimping members and the clip over an object to be clipped, and retracting the feeder of the clip applier simultaneously and continuously while the closure member is extending and until the closure member closes the crimping members. The closure member is retracted to open the crimping members to release the clip and the feeder of the clip applier is extended simultaneously and continuously while the closure member is retracting and until the closure member fully opens the crimping members.

In another aspect of the present invention, a method of manufacturing a jaw of a clip applier provides grinding a side profile of a jaw into a plate and machining the plate to form an entry point for clips on a proximal end of the jaw. The method further provides machining the plate to form grooves for clips along an inner surface of each crimping member of the jaw up to substantially near a distal end of the jaw, hardening the plate, and cutting a top profile of the jaw by using an electrical discharge machine.

Another method of manufacturing a jaw of a clip applier in yet another aspect of the present invention provides hardening a steel block, cutting at least one top profile of at least one jaw into the block, and leaving the at least one jaw attached in a rear portion to a portion of the block using an electrical discharge machine. The method further provides patterning a shape of interior grooves in the at least one jaw, burning the pattern into the at least one jaw using the electrical discharge machine, and detaching the jaw from the block using the electrical discharge machine.

In one example application of aspects of the present invention, a clip applier is utilized for ligating and occluding various sized vessels, other tissues or a previously applied clip or object and is capable of inserting a surgical clip through a cannula while minimizing the width or diameter occupied by the applier. A surgical clip, in one aspect, is generally U-shaped or V-shaped with a pair of outwardly extending and generally opposed legs connected at an apex.

Many of the attendant features of the present invention will be more readily appreciated as the same becomes better understood by reference to the following detailed description and considered in connection with the accompanying drawings in which like reference symbols designate like parts throughout.

BRIEF DESCRIPTION OF THE DRAWINGS

FIG. 2B illustrates a perspective view of one embodiment of a jaw;

DETAILED DESCRIPTION

Figure 1:
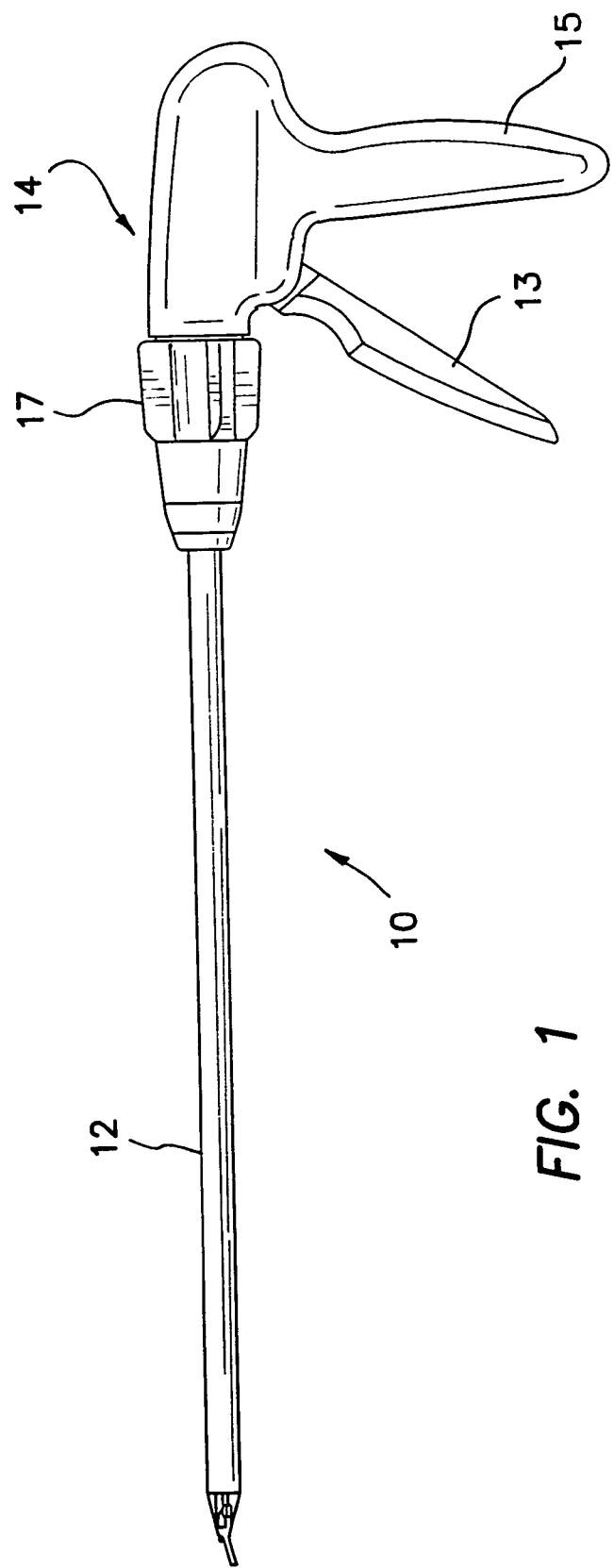
FIG. 1 illustrates a clip applier having a cartridge and an actuator in accordance with one embodiment of the present invention.

In FIG. 1, a laparoscopic clip applier 10 in accordance with one embodiment of the present invention is shown. The clip applier 10 is useful for endoscopic or a minimally invasive surgery. Clip applier 10 includes a disposable cartridge 12 and an actuator 14 connected to the disposable cartridge 12. The clip applier 10, in one embodiment, utilizes a two-way ratchet mechanism without delay and maintains a simplified construction in both the cartridge 12 and actuator 14. As a result, the clip applier 10 containing fewer parts is easier to sterilize and is less expensive to produce. Also, the clip applier 10 being partly or fully disposable, in another embodiment, the cartridge 12 and/or the actuator 14 do not need to be constructed of long lasting materials.

Generally, in operating the clip applier 10, a user completes a full actuating stroke advancing trigger 13 towards handle 15 of actuator 14 until a ratchet engagement releases and trigger 13 is allowed to return to its original position without impediment. The ratchet engagement will be described later in greater detail below. After the engagement releases, a user is permitted to release a partially crimped clip, if desired, or release a fully crimped clip. After release of a clip and once the engagement is re-engaged, the clip applier returns to its original position before another full actuating stroke can be performed. As such, the negative effects of unintended clip application, e.g., improper clip closing, clip releasing or clip feeding, are reduced.

The actuator 14 also includes a collar 17. In one aspect of the present invention, the collar 17 is rotatable about the actuator 14 that allows the position of disposable cartridge 12 to be reoriented as desired during use. In particular, through cantilever arms extending from collar 17 engaging slots in the cartridge 12 or a frictional engagement of the collar 17 with the cartridge 12, a rotational force applied to collar 17 is transmitted to cartridge 12 thereby rotating cartridge 12.

Figure 2A:
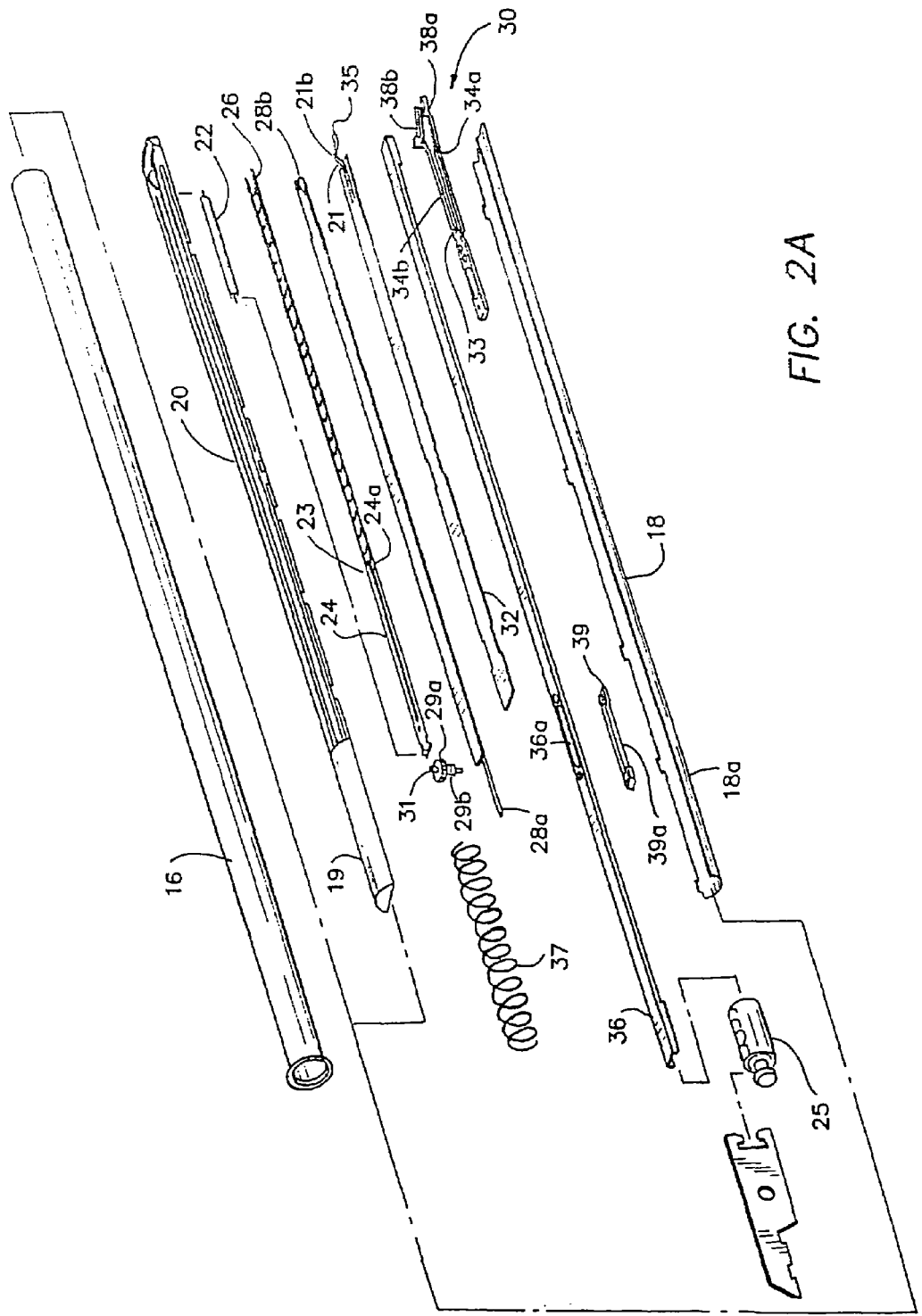
FIG. 2A illustrates an exploded view showing the assembly of the components of or connected to the cartridge.

FIGS. 2-7 illustrate further features of construction and operation of the clip applier 10. Referring now to FIG. 2, cartridge 12 includes a cover tube 16 that holds bottom housing 18 and a top cartridge 20. A pusher spring 22 is connected at its distal end to top cartridge 20 and at its proximal end to a pusher 24. The proximal end of pusher 24 has a pushing surface 24a that conforms to a clip 26. A series of clips 26 can be stacked end-to-end in front of pushing surface 24a; however, it is viewed that the scope of the invention is broad enough to include a cartridge that applies one or more clips in sequence.

A last clip follower 23, in one embodiment, is slidably mounted to the pusher 24. The distal end of the last clip follower 23 conforms to a clip 26 and the proximal end conforms to the pushing surface 24a. An extension member extends from an apex portion of the proximal end of the last clip follower along a channel in the pusher 24. A tab extends perpendicularly from the extension member through a slot in the pusher 24. The pusher 24 traverses distally due to pusher spring 22 and as clips 26 are applied, the pusher and last clip follower moves closer to the distal end of the cartridge 12.

If the actuator 14 is further utilized after the last clip has been applied, the last clip follower being mounted on the pusher 24 is prevented from being fed for application. The slot in the pusher 24, however, allows the last clip follower to continue to travel distally. Until contact is made by the tab on the last clip follower on the distal end of the slot, the last clip follower continues to travel and thereby prevents the last clip follower from jamming the cartridge after the last clip is expended.

Clips 26 rest on a feeder 28 as does pusher 24 while feeder 28 rests on cartridge floor 32. The distal end of feeder 28 comprises a feeder surface 28b that, similar to pushing surface 24a, conforms to the shape or an apex portion of a clip 26 to further advance the clips. The cartridge floor 32 includes a finger 21 that holds the next clip to be fed in place while the current clip is fed distally to jaw 30. In one aspect of the present invention, the floor 32 also includes a clip stop 35 that prevents the current clip from retreating back into the cartridge 12 from jaw 30.

The jaw 30 disposed partially in the cartridge 12 has a pair of opposed tapered surfaces 34a and 34b at the distal end of an elongated slot 33. Mounted or extending distally to tapered surfaces 34a and 34b are jaw members or crimping members 38a and 38b, respectively. Jaw 30 is mounted onto posts extending from bottom housing 18.

In one embodiment, the crimping members 38a and 38b include jaw tips (FIG. 2B) that are "bone shaped" to allow for better clip closure and visualization of the clip in the jaw 30. Better clip closure, in one embodiment, is achieved by thinning out the jaw tips allowing them to flex. This flexing allows for full compression of the clip apex. For example, as the closure member 36 engages the tapered surfaces 34a and 34b which causes the crimping members 38a and 38b to move together, the thin jaw tips reduces resistance to movement of the crimping members together and thereby maximizes the force by the closure member to move the crimping members 38a and 38b together. Therefore, full compression of the clip from the legs to the clip's apex is permitted or facilitated by facilitating the movement of the crimping members 38*a,b* towards each other. Additionally, various views or perspectives of the clip within the jaw 30 are eased as less portions of the jaw are available to obstruct the view of the clip within the jaw 30. In one aspect, the jaw tips include rounded protrusions or bumps. The bumps are at the distal end of the tips and make the jaw a-traumatic, preventing potential damage to tissue and trocar seals.

Closure member 36 is mounted over jaw 30. Tapered surfaces 34*a* and 34*b*, however, extend through a distal opening in closure member 36. Closure member 36 is also mounted between bottom housing 18 and top cartridge 20 and translates longitudinally responsive to a force input communicated by actuator 14. Jaw 30 opens as the actuator 14 is relaxed enough to allow backward travel of the closure member 36. This arrangement is desirable for a user demanding ultimate control of clip closure, e.g., affecting a partially closed or fully closed clip, and clip release once a clip is at least partially closed.

Extending from the proximal end of feeder 28 is rack 28*a*. The rack 28*a* has a plurality of teeth that extend laterally from rack 28*a* and thus the feeder 28 is operatively connected to a top portion 29*a* of spur gear 29. A bottom portion 29*b* of spur gear 29 is smaller than the top portion 29*a* of the spur gear 29, in one aspect of the present invention. The bottom portion 29*b* of spur gear 29 engages a plurality of teeth on closure rack 39. The teeth on rack 39 extending laterally from rack 39 are in an opposite direction from that of the teeth on rack 28*a*. Rack 39 further includes two posts extending from either ends of the rack. Each post extends through an opening in closure member 36 to directly connect rack 39 to closure member 36. As such, a spring is not used or connected to rack 39 and thereby minimizing the complexity and number of parts in the cartridge 12. Additionally, the variability in force and timing and imposed tolerances to ensure proper clip placement such components add can be eliminated. A slot 36*a* in closure member 36 exposes rack 39 for permitting the bottom portion 29*b* of spur gear 29 to engage the teeth of rack 39.

A hemispherical trough 18*a* is disposed in bottom housing 18 that receives a corresponding hemispherical tab 39*a* that substantially extends along the length of rack 39. As closure member 36 traverses longitudinally, rack 39 slides along the trough 18*a*. Spring 37 surrounds a proximal portion of closure member 36 and is limited from moving distally by a tab on closure member 36.

In one aspect, the spur gear 29 is a compound gear that is two gears parallel to each other supported by spindle 31. The diameters and the number of teeth on each gear or upper and lower portions of the gear are different. The ratio of teeth and diameters of the gears or portions of the gears determine the degree of movement of the closure member 36 and feeder 28. Varying the ratio of teeth and diameters of the gears or portions of the gears may also accommodate different sized clips.

Figure 3:
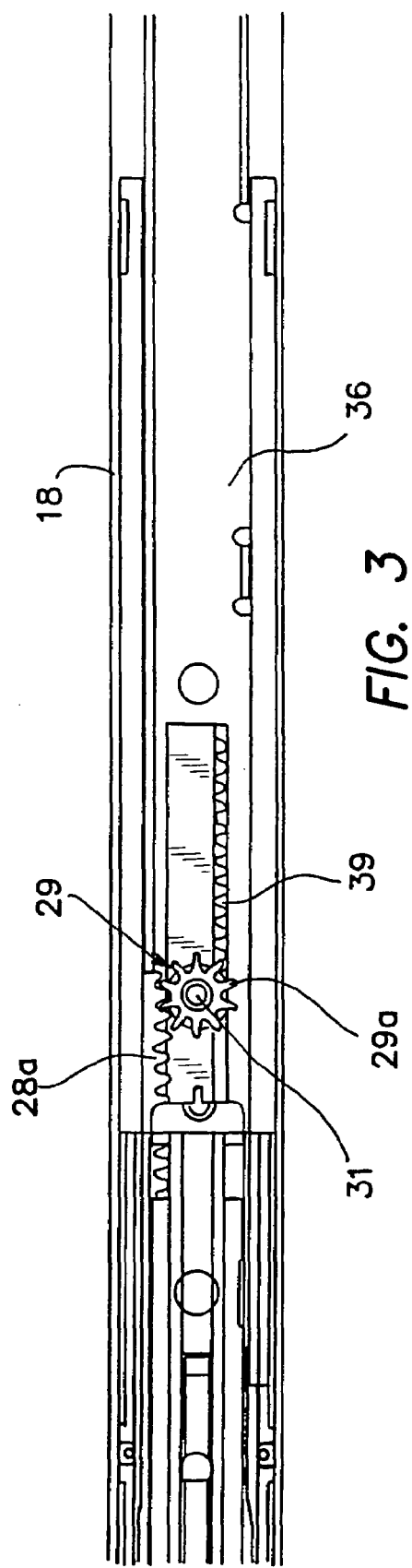
FIG. 3 illustrates an exploded view showing one embodiment of a rack mechanism in the cartridge.

Referring now to FIG. 3, the teeth of rack 28*a* engage substantially in the same plane with upper portion 29*a* of spur gear 29. Similarly, lower gear or lower portion 29*b* of spur gear 29 engages substantially in the same plane with the teeth of rack 39. Teeth of rack 28*a* face teeth of rack 39 on opposite sides of a longitudinal axis through cartridge 12 with teeth of rack 28*a* being in a higher plane than teeth of rack 39.

In one embodiment, one end of spindle 31 of spur gear 29 extends through an opening in a cover housing 19. The other end of spindle 31 extends through an opening in the bottom housing 18. The cover housing 19 is mounted on the proximal end of the bottom housing 18 via tabs on the bottom housing 18 inserted into corresponding recesses on the cover housing 19. The cover housing 19 and the bottom housing 18 secure the spindle 31 of the spur gear 29, but do not inhibit the rotation of the spur gear 29. As a result, accurate placement of the spur gear 29 to engage the rack 28*a* extending from feeder 28 and the rack 39 is facilitated, as is cartridge assembly.

Figure 4A:
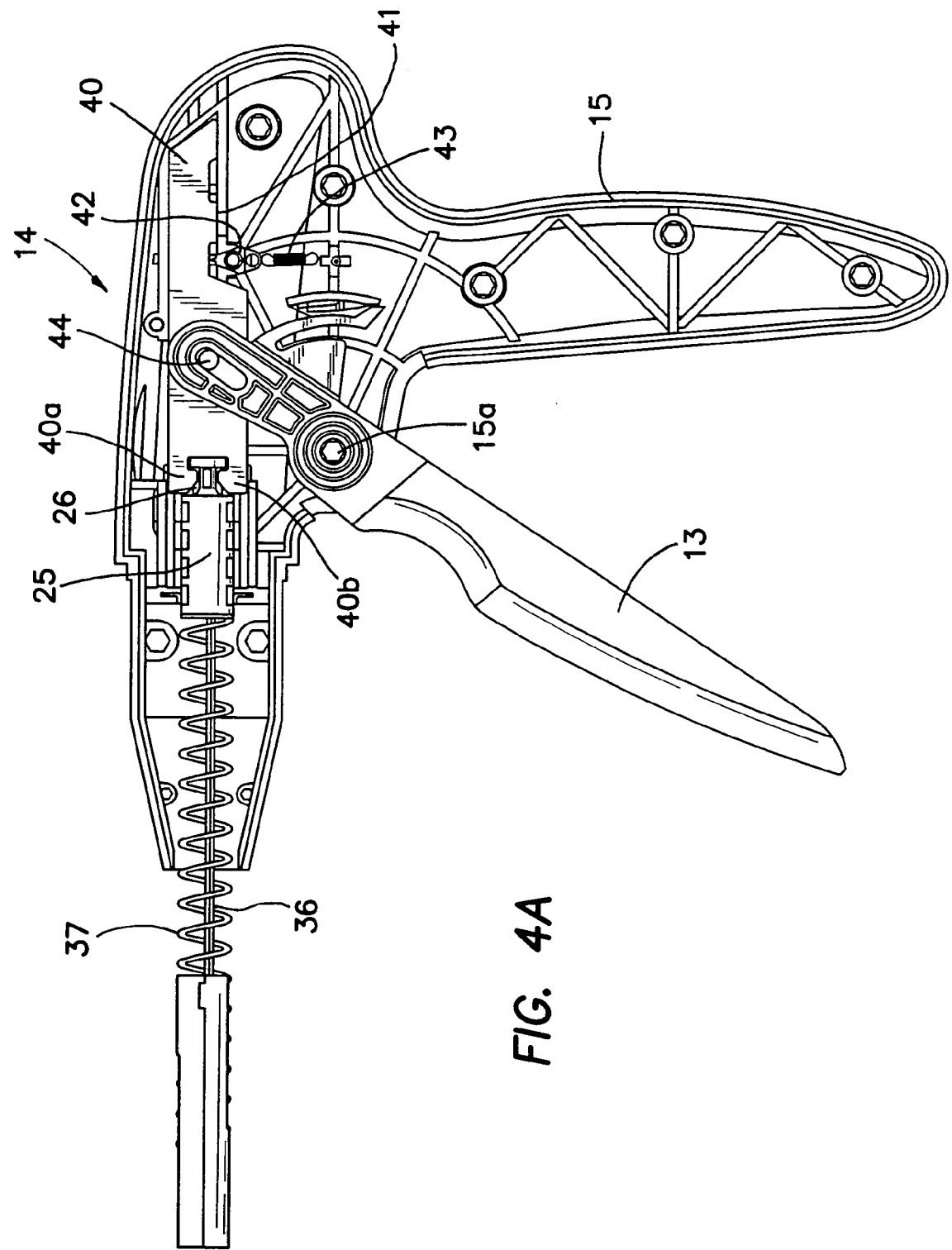
FIGS. 4A-4B illustrate one embodiment of an actuator.
Figure 4B:
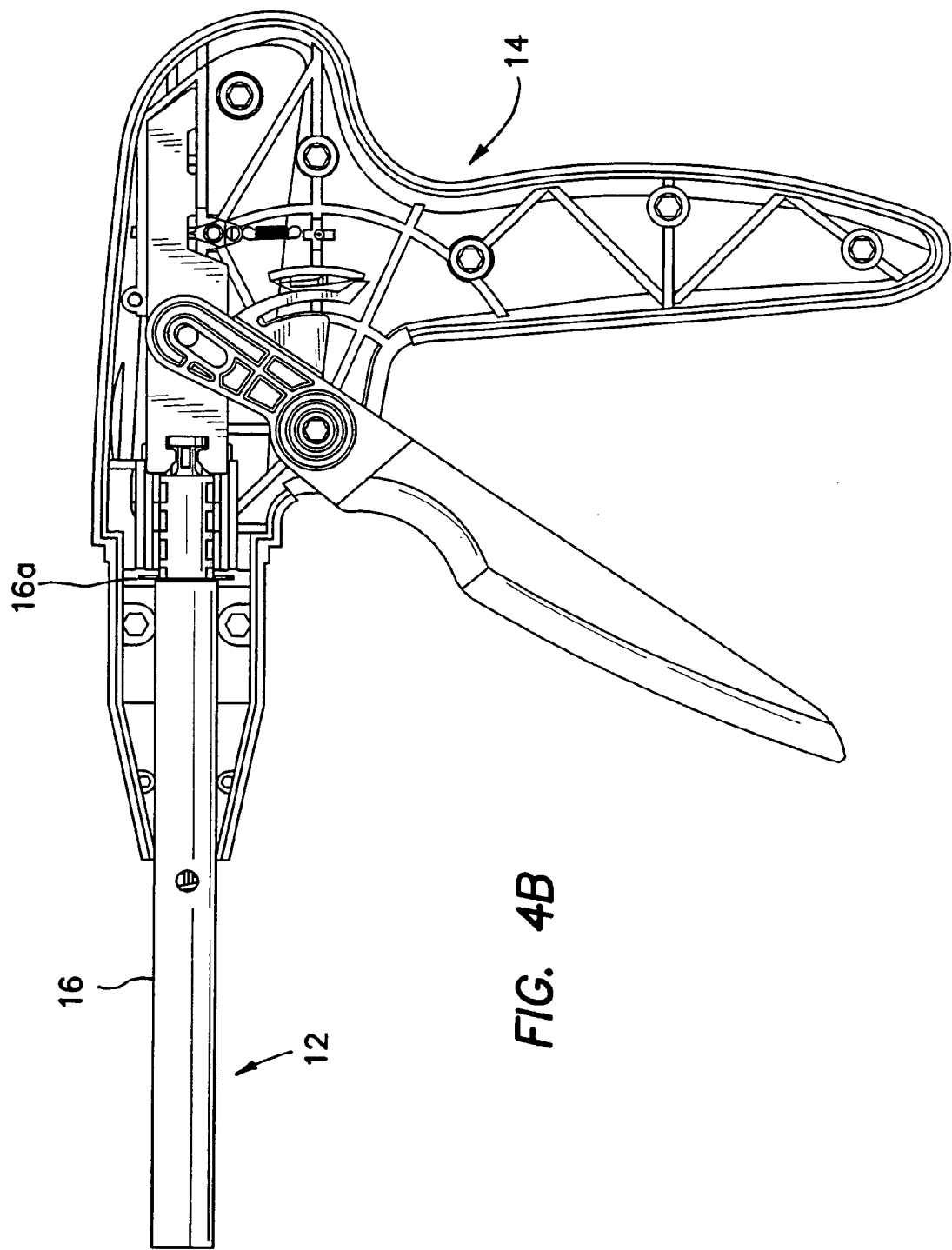

In FIGS. 4A-4B, one embodiment of actuator 14 (FIG. 1), and in one embodiment a disposable actuator, is shown. The proximal end of closure member 36 is connected to plunger 25 through a slot in the cylindrical portion of the plunger. A pin is inserted through the plunger 25 and closure member 36 to further secure the plunger 25 to the closure member 36. Plunger 25 biases spring 37 from moving proximally. In one embodiment, both the plunger 25 and the spring 37 are inserted through an opening in the actuator 14 and the collar 17 (FIG. 1). In operation, as force is applied to plunger 25, plunger 25 compresses spring 37 and causes closure member 36 to move longitudinally towards the distal end of the cartridge 12.

The proximal end of plunger 25 includes a circular notch 26 connected to driver 40 by arms 40*a* and 40*b* for permitting rotational movement of cartridge 12 as well as longitudinal movement of closure member 36 by driver 40. A circular tab 16*a* on the proximal end of tube 16 is confined in a slot formed in the actuator 14 and defines a diameter larger than the opening of collar 17 or actuator 14 and prevents longitudinal distal movement of tube 16.

Actuator 14 also includes trigger 13 and handle 15. Trigger 13 is connected to a post 15*a* on handle 15. When actuated, trigger 13 pivots around post 15*a*. Driver 40 rests between split tabs 13*a* and 13*b* (not shown) that extend from trigger 13. Pin 44 extends through a slot in split tab 13*a*, a hole in driver 39 and a corresponding slot in split tab 13*b* and is received into a slot on handle 15 to slidably connect driver 40 to the handle 15. A handle cover (not shown) also has a corresponding slot to receive pin 44 and to slidably connect driver 40 to the handle cover. In one embodiment, multiple apertures or posts on handle 15 able to receive respective posts or apertures on the corresponding handle cover provide for a snap fitting engagement of the handle 15 to the handle cover.

In one aspect of the present invention, driver 40 includes a rack region 41 having teeth that operatively engages pawl 42. Pawl 42 has three teeth. The middle tooth of pawl 42 extends further than the adjacent side teeth. A spring 43 on one end is connected to the pawl 42 and on the other end is connected to a post extending from the handle 15. A pivot pin extends through the center of pawl 42 and is inserted into corresponding apertures on handle 15 and the handle cover.

As trigger 13 is moved towards handle 15, driver 40 moves in the distal direction that causes pawl 42 to pivot and engage the teeth of rack region 41. Spring 43 biases pawl 42 to force pawl 42 securely into the teeth of rack region 41. This engagement, in particular, the middle tooth and one of the side teeth, the tooth on the side opposite to the travel direction of driver 40, with the rack region 41, permits distal movement of the driver 40 but prevents proximal movement of the driver 40.

Once the pawl 42 disengages from rack region 41, the spring 43 causes pawl 42 to pivot to a substantially upright position. Spring 37 compresses as the driver is moved distally, as previously described, and thus upon release of trigger 13, i.e., trigger 13 moves away from handle 15, spring 37 causes driver 40 to move proximally. Driver 40 traveling back causes pawl 42 to pivot and engage the teeth of rack region 41. Spring 43 biases pawl 42 to force pawl 42 securely into the teeth of rack region 41 to permit proximal movement of driver 40 but prevents distal movement of the driver 40 until pawl 42 once again disengages the rack region 41.

Therefore, when the trigger 13 is released, spring 37 will cause driver 40 to return to its original position without delay once pawl 42 first disengages the rack region 41. The rate at which driver 40 travels back distally, however, may be controlled by the amount of force or pressure exerted on trigger 13 as the trigger 13 is released. The operation and affect of the actuator 14 regarding clip feeding and clamping will be described later in greater detail below.

Figure 5A:
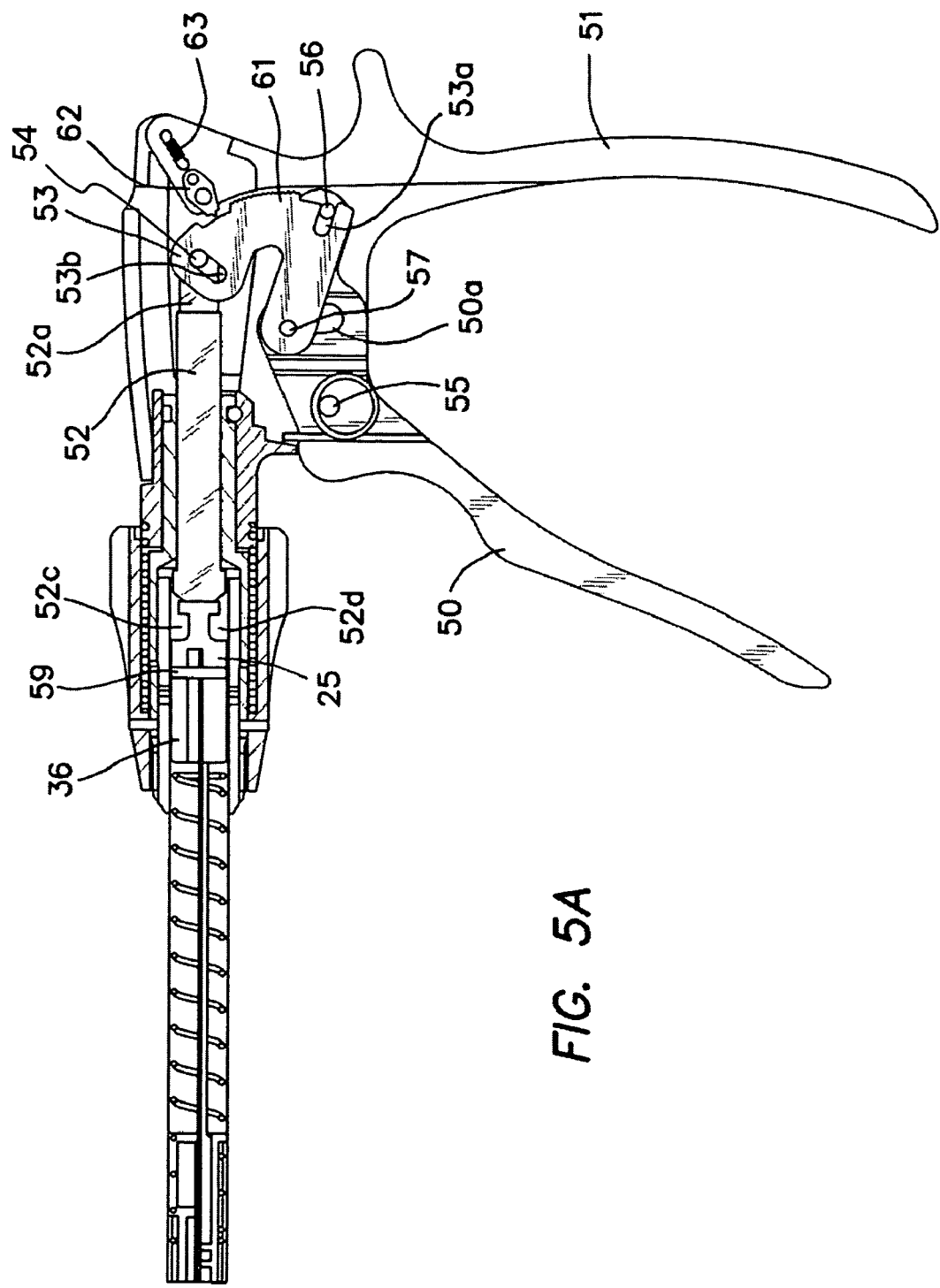
FIGS. 5A-5B illustrate another embodiment of an actuator.
Figure 5B:
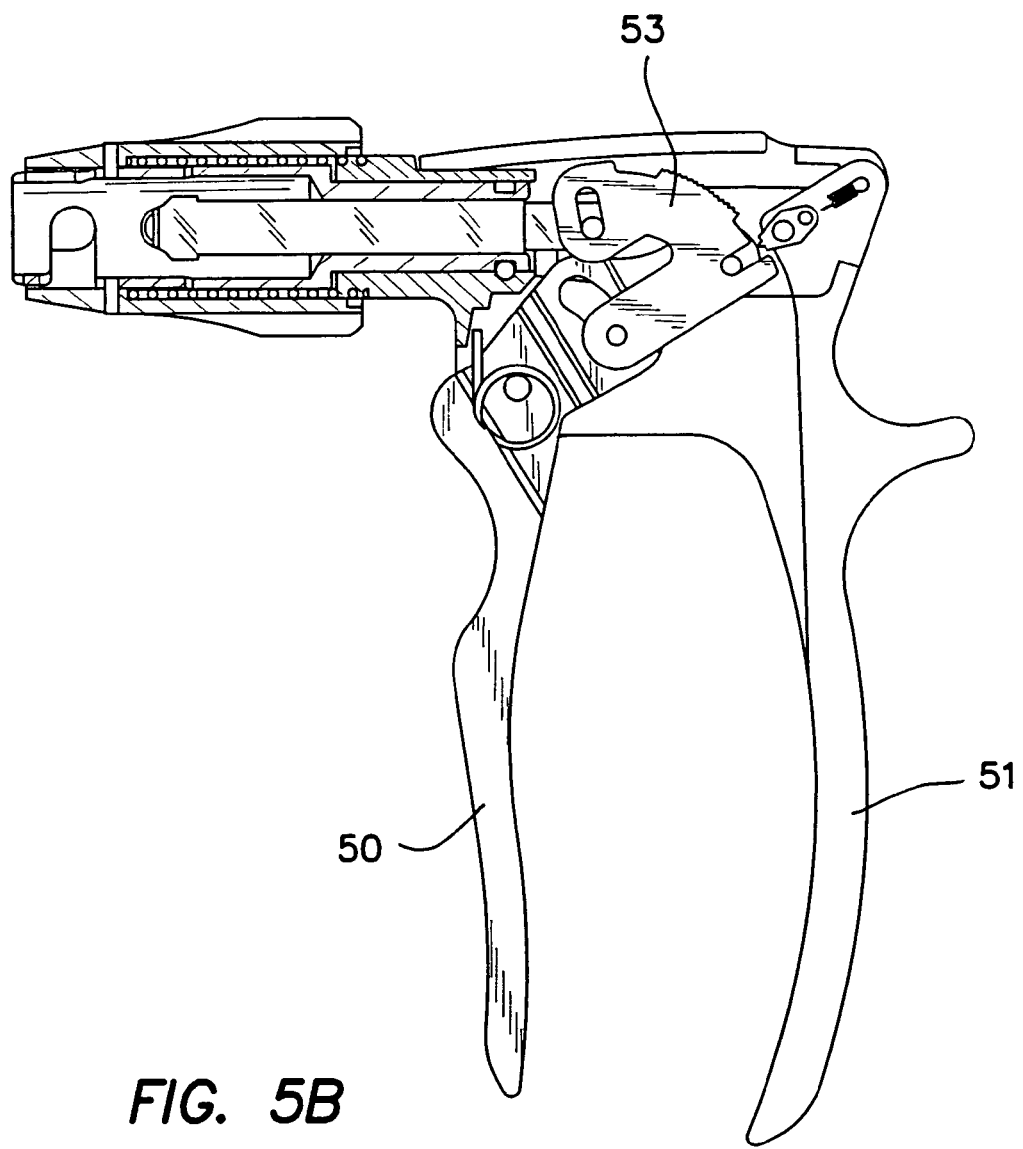

Referring now to FIGS. 5A-5B, another embodiment of actuator 14 of the present invention having a dual pivot cam mechanism is shown. The cam mechanism includes trigger 50 connected to pivot link 53. Rotational motion of trigger 50 rotating about post 55 on handle 51 is transmitted to pivot link 53 via pin 56. Pin 56 connected to the proximal end of trigger 50 is disposed within a slot 53a on pivot link 53. Pivot link 53 subsequently rotates about pin 57 that extends through opening 50a in trigger 50 and is connected to pivot link 53 and handle 51. As pivot link 53 is connected to driver 52 via pin 54 extending through an aperture 53b of pivot link 53, rotational motion of trigger 50 and pivot link 53 causes driver 52 to move linearly.

Post 55, a first pivot point, provides a natural or a comfortable stroke for advancing the trigger 50 towards handle 51. Pivot link 53 pivoting on pin 57, a second pivot point, shortens the rotational travel used to move driver 52 while still communicating the force on driver 52 as expected based on the actuation of trigger 50. However, the reduction of rotational travel minimizes the space utilized by the cam mechanism to move driver 52. Therefore, by providing two pivot points, a user may comfortably move the actuator without requiring additional force or losing any mechanical advantage and still permit a compact cam mechanism so that additional space in the actuator or a larger actuator is not required.

Driver 52, in one embodiment, includes two arms 52a and 52b (not shown) for connecting to pivot link 53. Pivot link 53 rests in a crevice defined between the two arms 52a and 52b. Pin 54 inserted through holes in arms 52a and 52b and an aperture 53b in pivot link 53 further secures the driver 52 to pivot link 53. Arms 52c and 52d on the distal end of driver 52 connect to a cylindrical notch in plunger 25 to interlock the driver 52 and plunger 25. Through this interlock, linear motion of driver 52 is communicated to plunger 25 and vice versa. However, rotational motion of the plunger 25 and in particular cartridge 12 (FIG. 1) that may occur during clip application is not communicated to driver 52. Plunger 25 moving distally also compresses spring 37 (FIG. 2A) and in turn distally moves closure member 36. Pin 59 secures plunger 25 to closure member 36.

Pivot link 53 includes a rack region 61 having teeth that operatively engages pawl 62 rotatably mounted on a pivot pin inserted into handle 51. Spring 63 operationally biases pawl 62 to force pawl 62 securely into the teeth of rack region 61. As trigger 50 is advanced towards handle 51, the middle tooth and one of the side teeth of pawl 62 permits distal linear movement of driver 52 and counter clockwise motion of pivot link 53 but prevents proximal linear movement of the driver 52 and clockwise motion of pivot link 53.

Once pawl 62 disengages from rack region 61 and trigger 50 is released, spring 37 (not shown) extends to cause driver 52 to move proximally. Driver 52 traveling back proximally causes pawl 62 to pivot and reengage the teeth of rack region 61. Therefore, the middle tooth and the other side teeth of pawl 62 permits proximal linear movement of driver 52 and clockwise motion of pivot link 53 but prevents distal linear movement of the driver 52 and counter clockwise motion of pivot link 53. Rack region 61, in one aspect of the present invention, may extend substantially along the surface area of pivot link 53 without operationally affecting the manipulation of actuator 14. An increased rack region 61 allows for an increase in spacing or size of the teeth of rack region 61 that eases sterilization of the actuator 14 and in particular rack region 61.

Figure 6A:
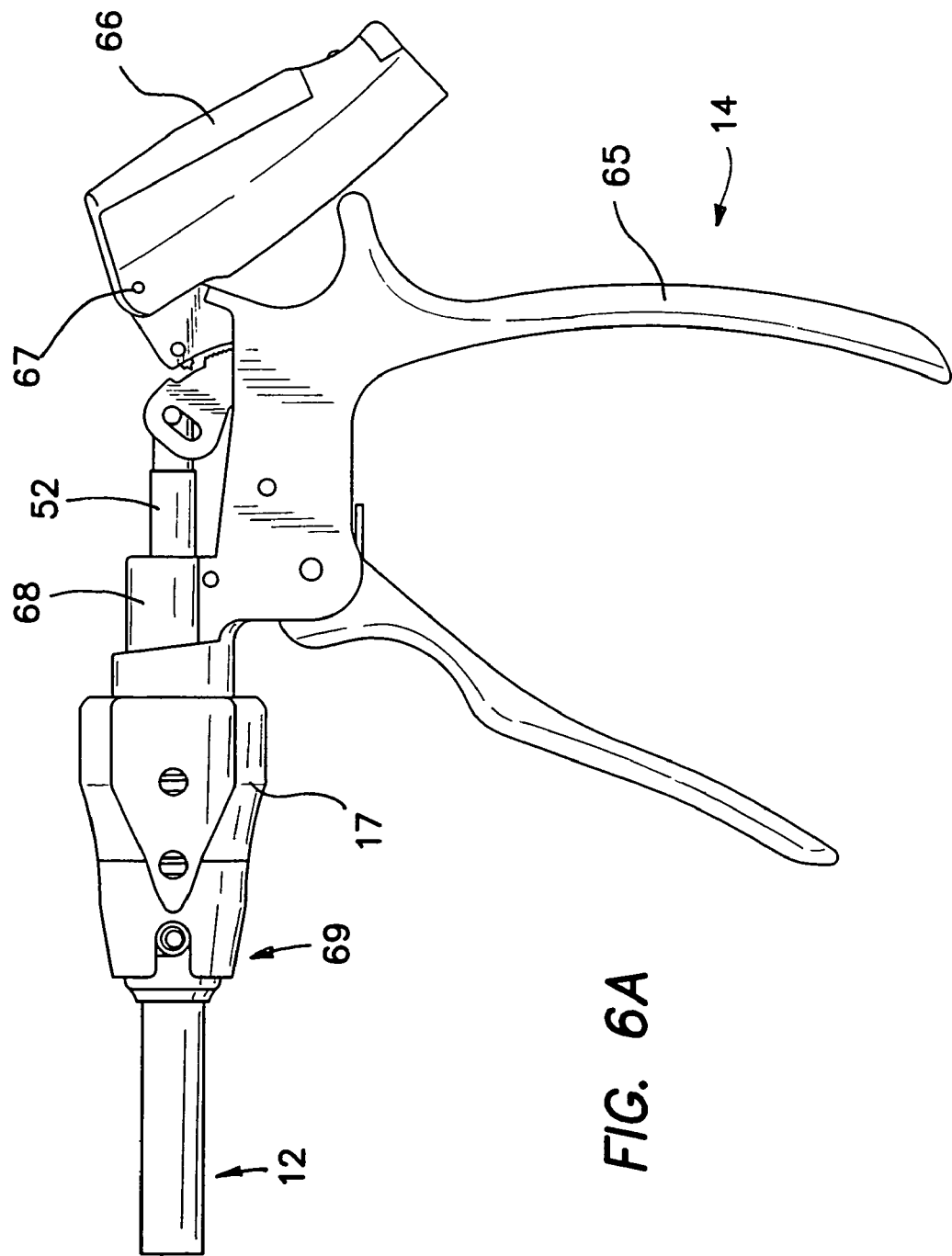
FIGS. 6A-6B illustrate embodiments of an assembled actuator of FIGS. 5A-5B.
Figure 6B:
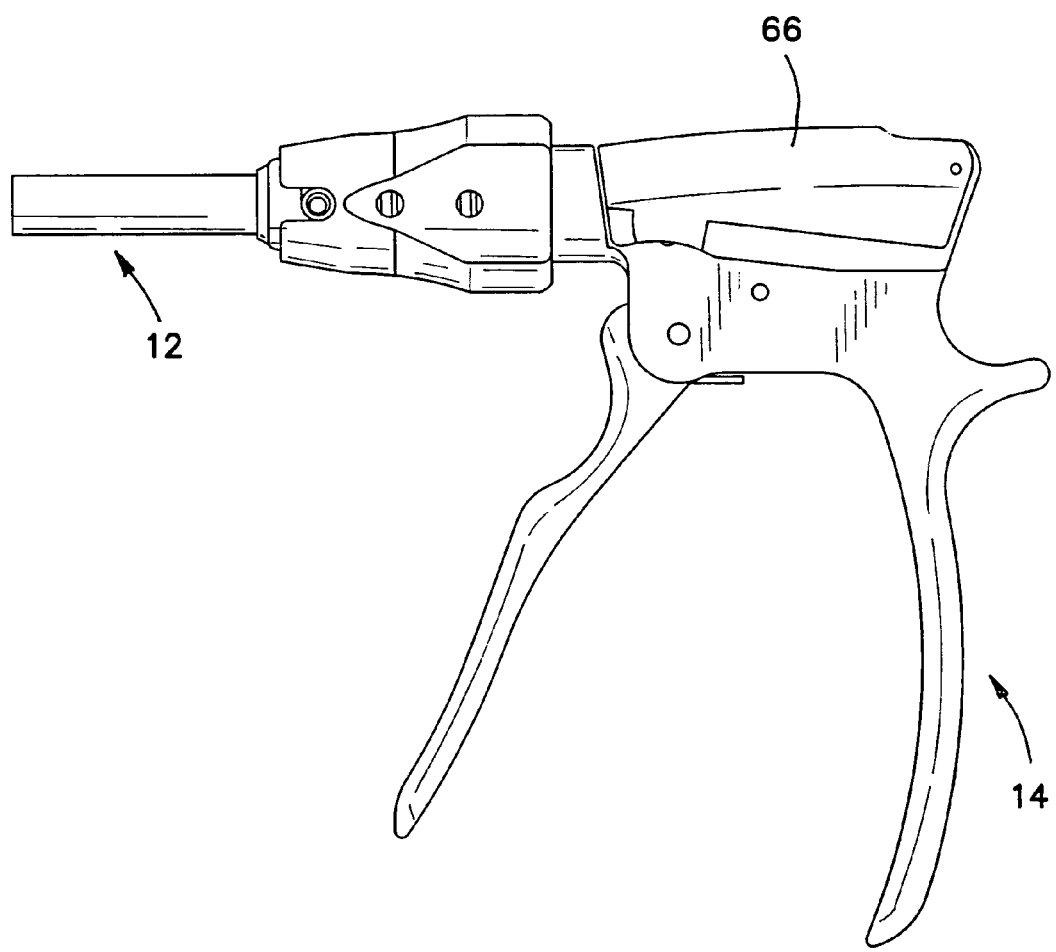

Actuator 14, in one embodiment, further includes a swing cover 66 as shown in FIGS. 6A-6B. As shown, the handle 51 is a single component housing portions of the trigger, the pivot link and other previously mentioned components. In another embodiment, the handle comprises a handle cover mounted onto a handle housing in which portions of the trigger, the pivot link and other previously mentioned components are disposed there between. Swing cover 66 rotatably connected to handle 51 protects the driver 52 and other components of the cam mechanism within a cavity disposed in swing cover 66. Swing cover 66, specifically, rotates about pin 67 and snaps onto a cylindrical boss 68. Swing cover 66 may also be rotated clockwise to expose the driver 52 and other components of the cam mechanism to facilitate sterilization of the actuator 14.

Through a bayonet type fitting 69, the cartridge 12 is longitudinally inserted into and connected to the actuator 14. In one aspect of the present invention, a longitudinal component of an L-shaped slot or slots on the actuator and passes by a pin or pins mounted on a cuff on the cartridge in which a spring disposed in the cuff compresses. The cartridge 12 is rotated to move the pin or pins along the radial component(s) of the L shaped slot or slots and the cuff spring is allowed to extend such that the cartridge is thereby secured to the actuator. A slide cuff may also be slidably connected to the actuator 14 and connected to the collar 17 for retracting to expose the slot or slots on the actuator 14 and for extending to cover and protect the fitting. In one embodiment, the collar 17 acts as a slide cuff.

In one aspect of the present invention, one or more extension members (not shown) may be disposed between the actuator 14 and the cartridge 12 to extend the reach of the clip applier 10. The extension members may be similarly fitted as described above to the actuator or cartridge. A rod is disposed in the extension member for communicating force applied by the actuator or from the cartridge. The rod, as such, in one embodiment, interacts with spring 37 (FIG. 2A) and includes a slot for receiving closure member 36.

Referring now back to FIGS. 1-6, clip feeding, crimping and releasing is discussed below in reference to cartridge 12 and the actuators previously described. By pressing trigger 13, closure member 36 traverses distally. As the closure member 36 moves in the distal direction, rack 39 connected to the closure member 36 also moves in the distal direction. With the closure member 36 moving distally, the teeth of rack 39 engage the lower portion 29b of spur gear 29 to rotate spur gear 29. As a result, the upper portion 29b of the spur gear 29 also rotates and engages the teeth of rack 28a extending from feeder 28 thereby causing feeder 28 to travel in the proximal direction or retract.

When closure member 36 moving distally advances against tapered surfaces 34a and 34b of jaw 30 pushing them together, a clip placed between crimping members or jaws 38a and 38b is also crimped as jaws 38a and 38b move toward each other. As such, a surgeon by actuating the trigger is in direct or full control of the crimping of the clip. The ratchet mechanism, e.g., the pawl 42 and rack 41 or the pawl 62 and rack region 61, in actuator 14 engage to permit continued pressure on trigger 13 while maintaining the position of the trigger if pressure is removed or reduced.

With feeder 28 retracting, pusher 24 due to force applied by pusher spring 22 is allowed to push the clips 26 forward moving the next clip in line to be fed and crimped. The arms of the next clip are guided by side ramps on top cartridge 20 and the bight portion of the next clip is angled by a middle ramp on the top cartridge 20 towards the cartridge floor 32. Further movement of pusher 24 distally and retraction of feeder 28 causes the next clip to dislodge from the clips 26, such that the pusher 24 no longer exerts longitudinal force on the next clip.

Figure 7A:
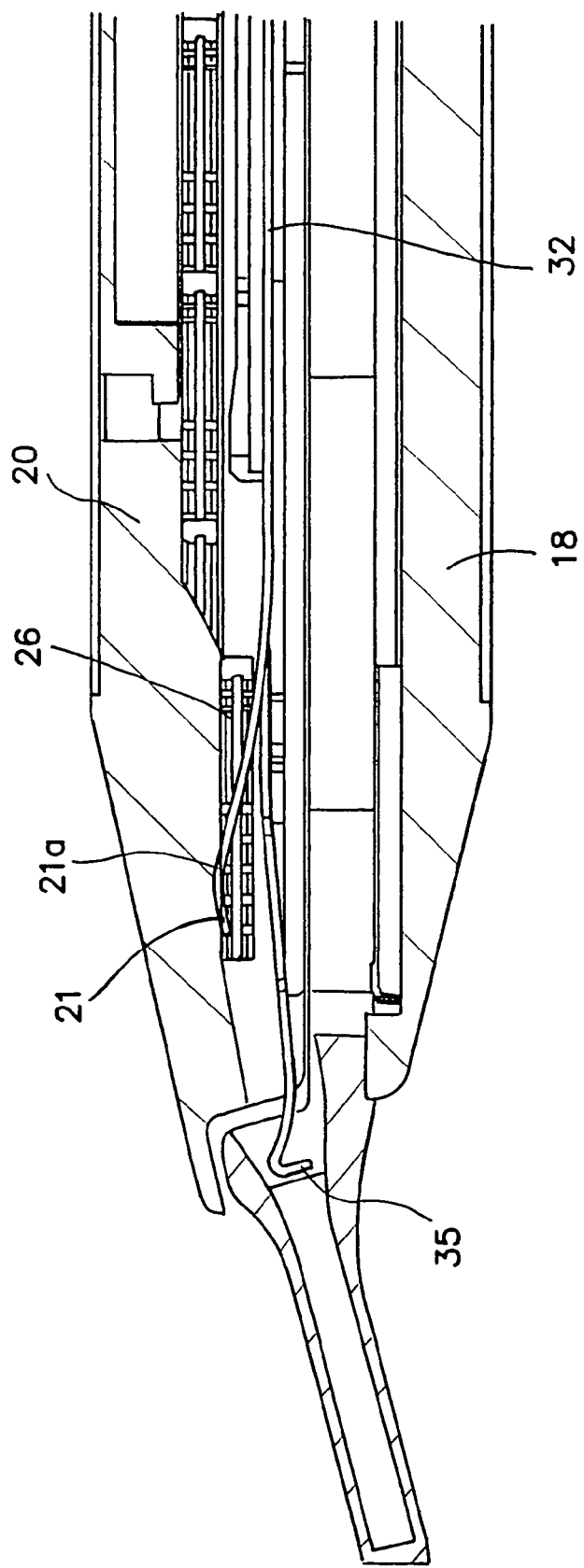
FIG. 7A illustrates a cross sectional view of one embodiment of the cartridge.
Figure 7B:
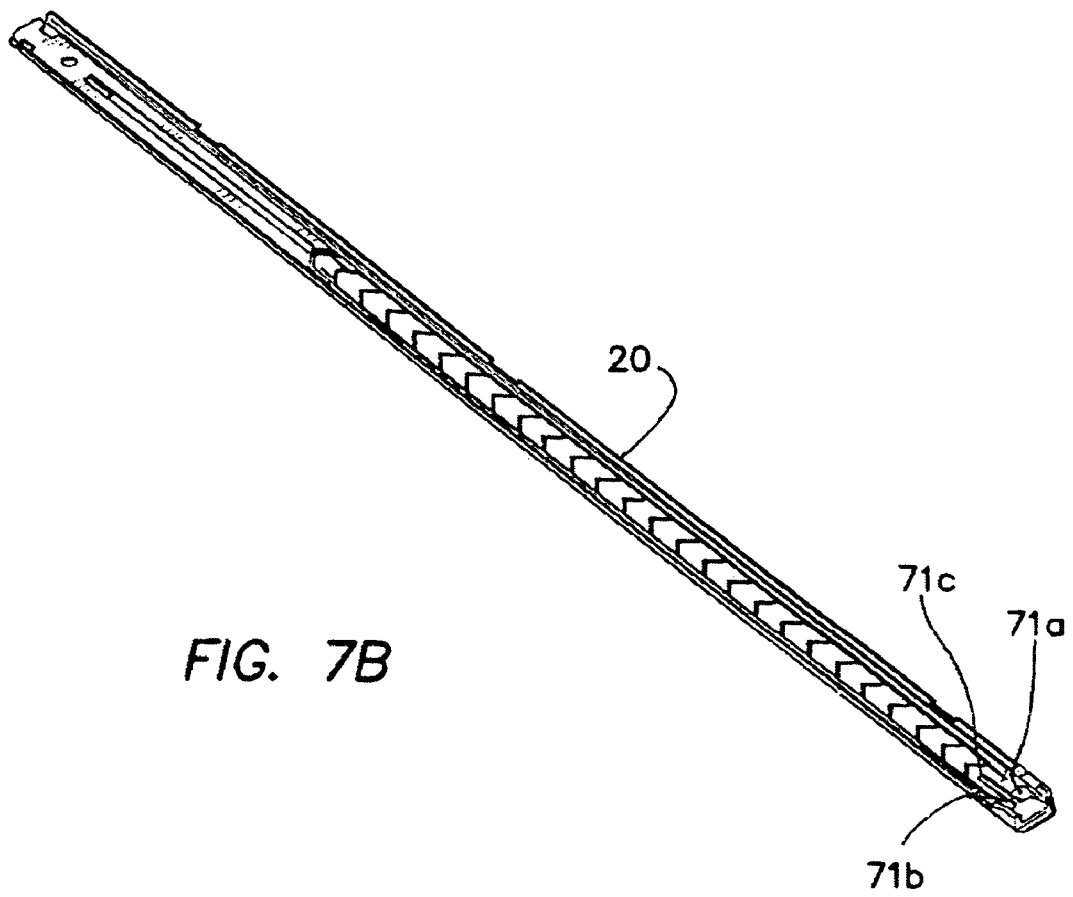
FIG. 7B illustrates one embodiment of a partially assembled cartridge.

Referring also now to FIGS. 7A-7B, the cartridge floor 32 includes a finger 21 with a peninsular cutout 21*b* (FIG. 2) and a portion angled 21*a* towards the top cartridge 20. Finger 21 along with side ramps 71*a* and 71*b* and middle ramp 71*c* of top cartridge 20 holds the next clip in position in preparation for feeder surface 28*b* on feeder 28 to contact the clip. The finger 21, in one embodiment, travels along a groove extending through the center portion of the feeder 28 as the feeder is extended and retracted to prevent interference of the finger 21 with the feeder 28 and yet maintain maximum retention of the next clip.

When the ratchet mechanism in actuator 14 disengages, as a full close actuating stroke is completed, continued pressure on the trigger 13 fully crimps the clip as jaws 38*a* and 38*b* continue to move towards each other. Subsequent removal of pressure on trigger 13 allows closure member 36 to retract. Jaws 38*a* and 38*b* thereby separate and the clip is released. In one embodiment, after a full closing actuating stroke is completed, a partially crimped clip is formed and thus removal of pressure on trigger 13 causes the partially crimped clip to be released.

Once the partially or fully crimped clip is applied and the closure member 36 is allowed to retract, the feeder 28 extends due to the rack mechanism in the cartridge 12, e.g., rack 39, rack 28*a*, and the spur gear 29 now rotating in the opposite direction. Feeder surface 28*b* of feeder 28 contacts the next clip to move it distally guided by finger 21. In particular, the arms of the next clip move along the sides of finger 21 and contact with the bight portion of the next clip causes the finger 21 to flex towards the bottom housing 18. As such, uneven contact or force applied by the feeder surface 28*b* of feeder 28 or a skewed position of the next clip is counter balanced by the peninsular cutout and angled portion of finger 21. Therefore, misalignment of the next clip is reduced as it is guided towards the crimping members 38*a* and 38*b* of jaw 30.

As the feeder continues to extend and the next clip travels distally, the clip clears the side ramps 71*a* and 71*b* of top cartridge 20, finger 21 and clip stop 35 and enters into grooves in the crimping members 38*a* and 38*b* of jaw 30. The grooves in the crimping members are offset of the longitudinal path of the feeder, causing the feeder to flex as the clip is advanced into the jaw 30. In one embodiment, the grooves are substantially in-line of the longitudinal path easing entry of a clip into the grooves of the jaw. The feeder 28 remains in direct contact with the advancing clip to ensure a substantially constant surface to maintain alignment of the next clip as it is moved into the crimping members 38*a* and 38*b* of the jaw 30. Clip stop 35 prevents the next clip, now the current clip, from moving proximally which may interfere with other clips being fed when feeder 28 once again retracts.

As the closure member 36 retracts, the crimping members 38*a,b* are allowed to open or move away from each other. The distance and rate at which the second rack 39 retracts substantially corresponds to the distance and rate in which the closure member 36 retracts since the second rack 39 is directly connected to the closure member 36. Through the interaction of the spur gear 29 with the first and second racks, the rate and, in one embodiment, the distance at which the first rack 28*a* extends substantially corresponds to the rate and, in one embodiment, the distance in which the second rack 39 retracts.

With the first rack 28*a* extending from or otherwise directly connected to the feeder 28 and the closure member 36 being directly connected to the second rack 39, the rate and, in one embodiment, the distance at which the feeder 28 extends also corresponds to the rate and, in one embodiment, the distance at which the closure member 36 retracts. This direct contact and interaction between racks ensures that the feeder 28 advances the clip to be placed between the crimping members 38*a,b* at a substantially identical rate at which the closure member 36 allows the crimping members 38*a,b* to open. As a result, the crimping members 38*a,b* are sufficiently open or apart to receive the advancing clip at substantially the same time in which the advancing clip is being advanced between the crimping members 38*a,b*.

In other words, the feeder 28 advances a clip as the crimping members 38*a,b* are being moved apart and advances the clip into the crimping members 38*a,b* as the crimping members 38*a,b* become sufficiently open. Thus, forcing a clip into a closed or not sufficiently open jaw 30 or jamming an advancing clip within the cartridge 12 because the jaw 30 is closed or not sufficiently open to release a previous clip and/or receive a new clip is avoided. As such, without imposing additional requirements, components or reducing tolerances, the timing between the placing of the clip between the jaw 30 of the clip applier after the jaw 30 is sufficiently open to properly receive the clip and before a user attempts to crimp the clip is adhered to and ensured.

Additionally, components to lock out or interrupt advancement of the feeder 28 to place a clip into the jaw 30 before the jaw 30 is sufficiently opened are avoided. Components to quickly and forcibly move the feeder 28 faster than the closure member 36 and vice versa, e.g., a spring-loaded feeder or racks, to ensure that the jaw 30 is sufficiently open are also not used. Therefore, the rapid operation of applying multiple successive clips is not hindered or slowed and complicated mechanical assemblies or components to affect the feeder 28 or the closure member 36 are avoided.

After completing a full close actuating stroke, as the feeder 28 extends, the ratchet mechanism in actuator 14 re-engages to prevent any pressure on trigger 13 from executing another full close actuating stroke before the trigger 13 returns to its original initial position, i.e., a full open actuating stroke is completed. The closure member 36 being connected to the feeder 28 and the ratchet mechanism in the actuator 14 ensures that the trigger 13 may not be actuated until the next clip is advanced sufficiently into the jaw 30. Therefore, the next clip is moved between the crimping members 38*a,b* before a user is permitted to actuate the trigger 13 to crimp the clip. The rate at which the open actuating stroke is completed may be controlled by pressure on trigger 13. However, the ratchet mechanism does not maintain the position of trigger 13 if pressure is removed or reduced. Spring 37 acting on driver 40 (FIGS. 4A-4B) or driver 52 (FIG. 5A-5B) in particular forces trigger 13 back to its original initial position.

The rack mechanism of cartridge 12 and the ratchet mechanism of actuator 14 can be made with strong, compact and reliable components. In one aspect of the present invention, for example, the actuator shown in FIGS. 5A-6B, may be made of durable and reusable components capable of withstanding numerous operations and sterilization processes using chemicals and/or high degrees of temperature.

In another aspect of the present invention, the rack and ratchet mechanisms may be made with less bulky and lighter components than metal components and may be disposable. For example, the embodiments of the present invention can be implemented by incorporating molded plastic parts. In one embodiment of the present invention, gamma radiation resistance and lubricious characteristics would be useful. Viable resin candidates having the above characteristics include, among other materials, glass-filled nylon, liquid crystal polymers, and PEEK. Other plastics such as polyurethane, polyester, polycarbonate, polysulfone and polyetherimide in the high durometer range are also capable choices. In one application of the present invention, the rack mechanism of cartridge 12 is small enough to fit within the constraints of a 10 mm diameter cartridge barrel.

In one embodiment, an electrical discharge machine (EDM) is used to manufacture the jaw 30. An EDM, in one aspect, is used to manufacture the jaw because it allows for a wide range of material thickness on a single part. In other words, varying cross-sections in multiple directions are permitted or available in manufacturing the jaw 30. An EDM also allows for consistent material properties. With other methods of manufacturing such as stamping the part is manufactured from one material thickness and thus varying ranges of material thickness throughout the part, e.g., the jaw, can prove difficult. In addition, stamping is a cold working process, which can create areas of high stress near bends or other areas where the metal has been formed. This may create an inconsistent part and can lead to breakage in the areas of high stress.

Figure 8A:
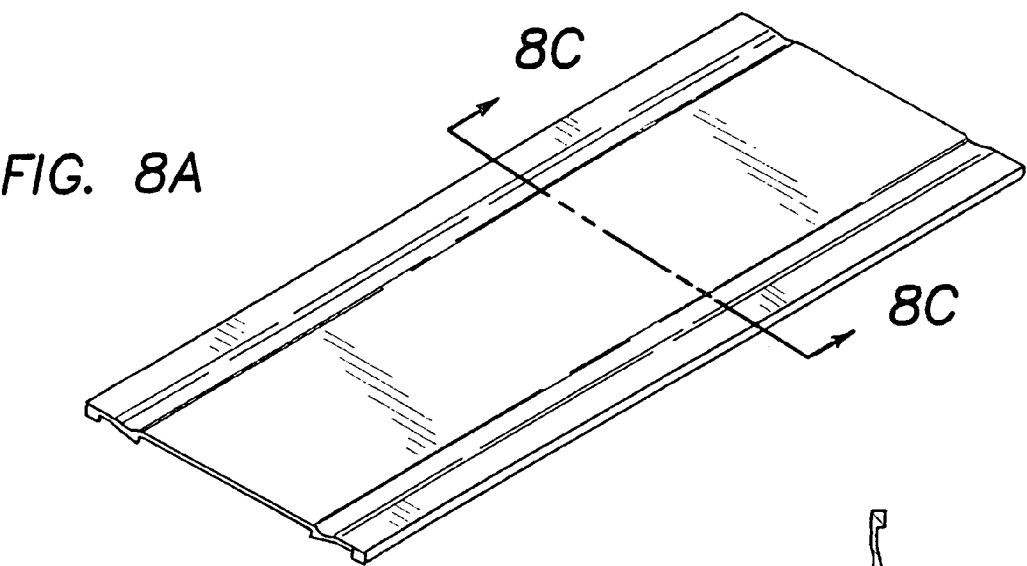
FIGS. 8A-C illustrate one embodiment of a plate used for manufacturing an embodiment of a jaw or jaws of the present invention.
Figure 8C:
Figure 8B:
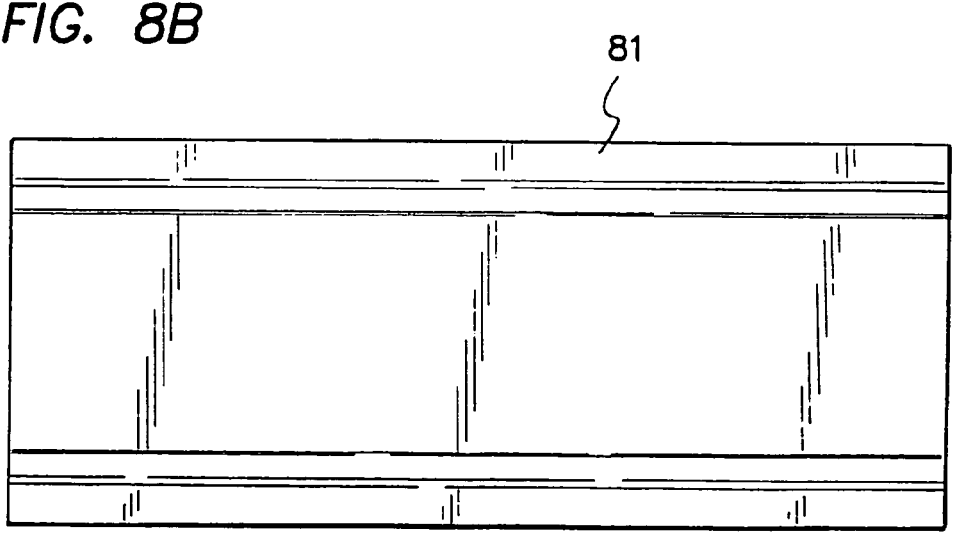
Figure 9:
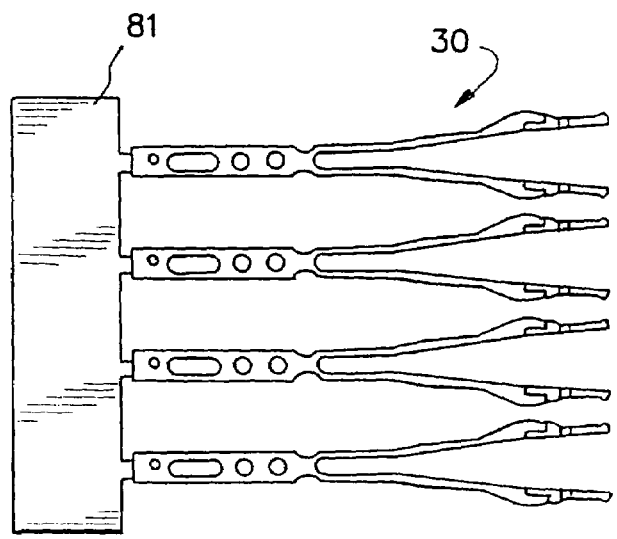
FIG. 9 illustrates one embodiment of jaws being formed from a plate in accordance with one aspect of the present invention.

In one aspect, as shown in FIGS. 8-9, the jaw's side profile is ground into a plate 81, such as a 5"×12" 400 series stainless steel plate. The plate is machined to achieve the clips entry point and a groove for the clip to travel to the distal end of the jaw 30. Once the machining has been completed, in one embodiment, the plate is stamped to acquire three location holes. The plate is heat treated for hardening. Once hardened, in one embodiment, the jaw's top profile is cut with the use of Electrical Discharge Machines (EDM). In one aspect, the use of EDM per plate yields 33 jaws. These jaws are centrifugally tumbled for the purpose of breaking all sharp edges, passivated, blackened & baked with a Teflon based material that provides a lubricous surface for a clip to slide on once in the groove.

Figure 10A:
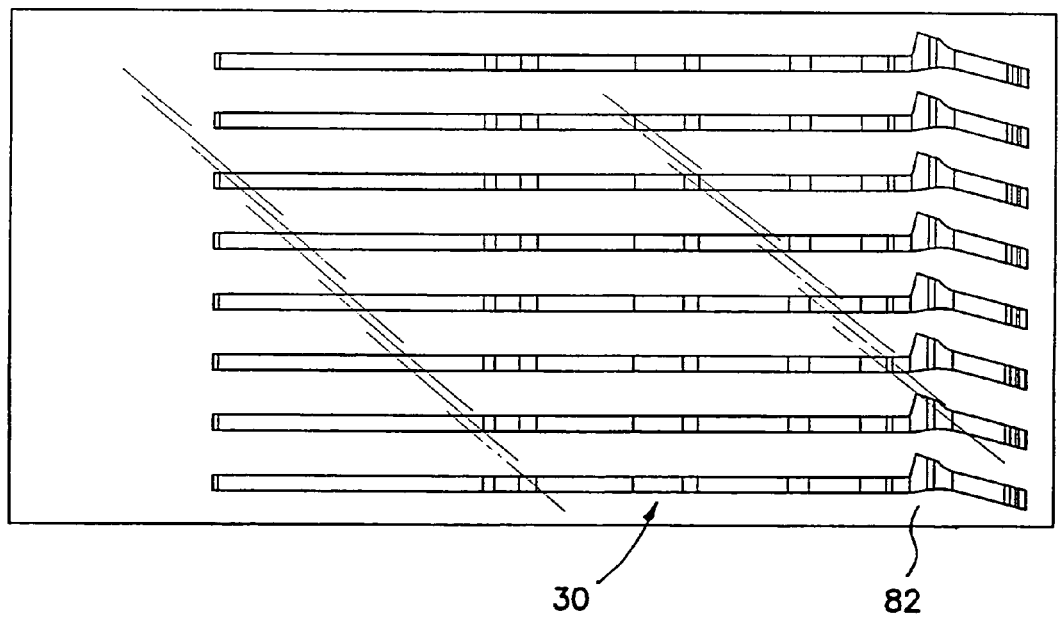
FIGS. 10A-C illustrate one embodiment of jaws being formed from a steel block in accordance with one aspect of the present invention.
Figure 10B:
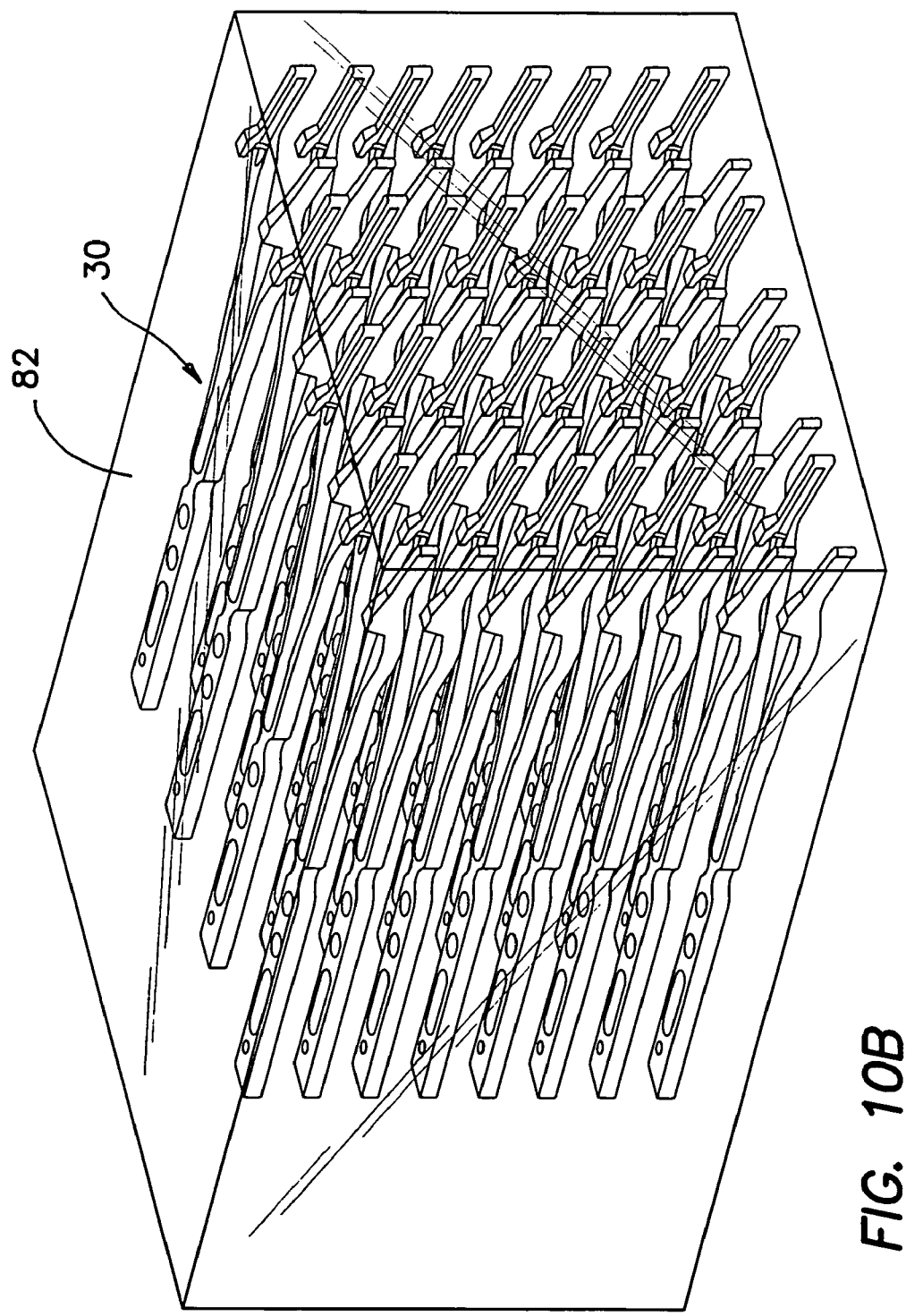
Figure 10C:
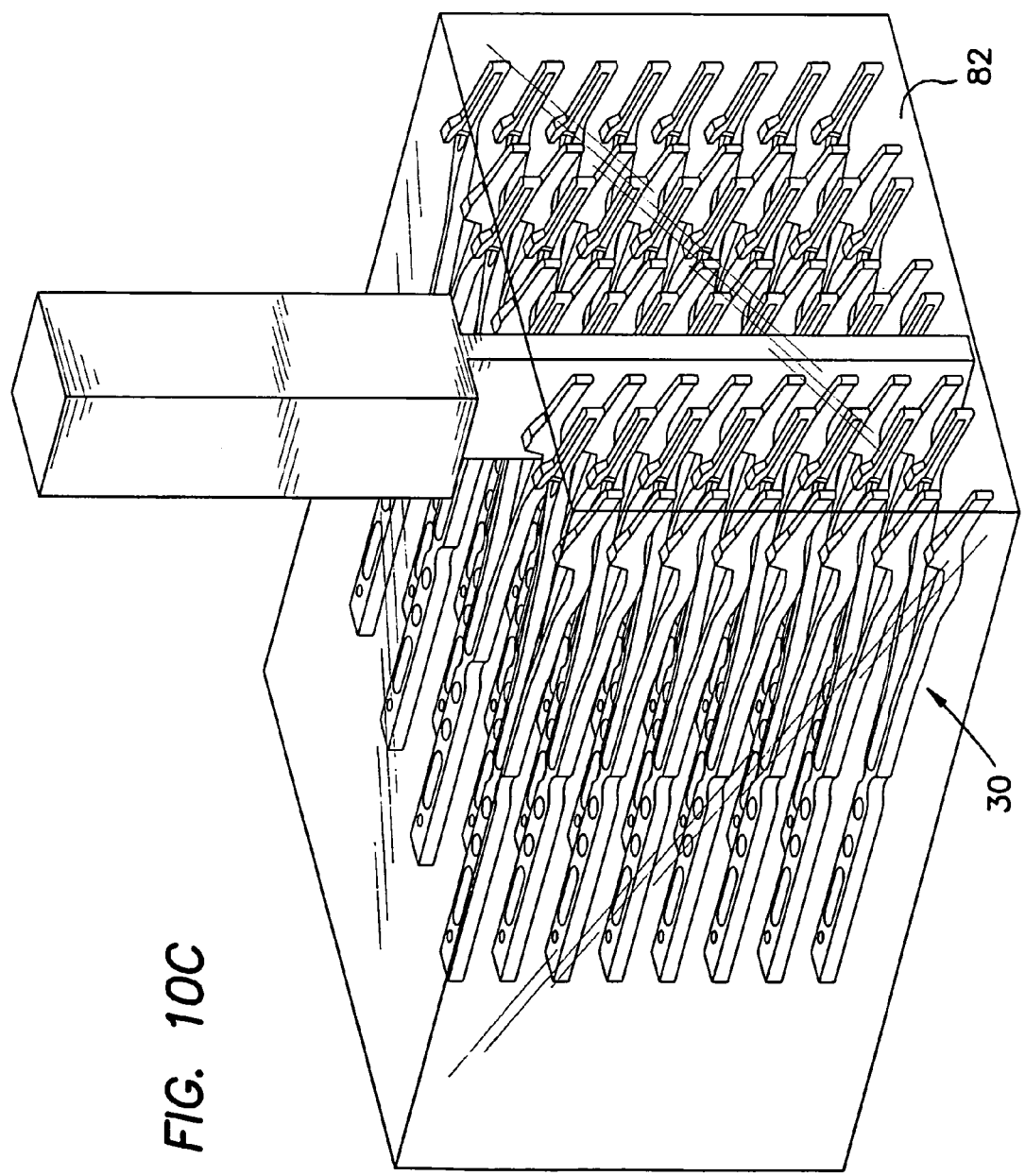

In one embodiment, as shown in FIGS. 10A-C, a full EDM jaw 30 is manufactured from a solid block 82 of stainless steel, e.g., 400 series stainless steel. The steel block is heat treated to a state of maximum hardness. The top profile of the jaw is Wire EDMed from the block, leaving the jaw attached in the rear portion. To form an interior groove portion, a pattern is created to the shape of the interior groove and used to EDM plunge or "burn" the grooves into the jaw. The top profile is Wire EDMed from the block, leaving a complete, hardened jaw. Profiles can be grouped together to cut multiple jaws from a single block.

Accordingly, the present invention provides fully controllable multi-fire clip appliers and methods thereof. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. A clip applier for applying a surgical clip, the applier comprising:
   a cartridge with a proximal end and a distal end and including:
      a feeder having a proximal end and a distal end,
      a closure member having a proximal end, a distal end, and a slot formed therein,
      a pair of symmetrical opposing crimping members extending outwardly from the distal end of the closure member, and
      a rack mechanism having a spur gear disposed on a spindle, a first rack connected to the feeder, and a second rack connected to the closure member, wherein the spindle extends through the slot in the closure member such that the spur gear interfaces with the second rack; and
   an actuator coupled to the proximal end of the cartridge and the proximal end of the closure member, the actuator arranged to open the opposing crimping members during an opening stroke and the closure member and the second rack arranged to move synchronously throughout the opening stroke.

2. The clip applier of claim 1 wherein the closure member and one of the feeder, the first rack and the second rack are all only movable together.

3. The clip applier of claim 1 wherein the second rack is arranged to only move at rates that substantially corresponds to rates at which the closure member moves.

4. The clip applier of claim 1 wherein the second rack moves synchronously with the closure member throughout operation of the closure member.

5. The clip applier of claim 1 wherein the feeder and the closure member arranged to travel at substantially identical rates throughout the opening stroke.

6. The clip applier of claim 1 wherein the second rack maintains constant contact with closure member.

7. The clip applier of claim 1 wherein the second rack is not prevented from moving while the closure member is moving.

8. The clip applier of claim 1 wherein the actuator is arranged to advance and retract the closure member and the rack mechanism correspondingly retract and advance the feeder at substantially identical rates at which the closure member moves.

9. The clip applier of claim 1 wherein the crimping members have jaw tips that are bone shaped.

10. The clip applier of claim 9 wherein the jaw tips are thin relative to the crimp.

11. The clip applier of claim 1 wherein the crimping members are manufactured using an electrical discharge machine.

12. The applier of claim 1 further comprising a ratchet mechanism comprises a third rack including teeth and a pawl having three teeth wherein at most two of the three teeth operatively engage the teeth of the third rack.

13. The applier of claim 12 wherein the three teeth of the pawl comprises a middle tooth, a first side tooth and a second side tooth, the middle and first side tooth operatively engaging the teeth of the third rack as the third rack traverses in a first direction and the middle and second side tooth operatively engaging the teeth of the third rack as the third rack traverses a second direction, the second direction being in an opposite direction from the first direction.

14. The applier of claim 13 wherein the spur gear is operatively connected to the first and second racks to move the feeder proximally when the closure member moves distally and the third rack moves in the first direction and to move the feeder distally when the closure member moves proximally when the third rack moves in the second direction.

15. The applier of claim 13 wherein the pawl is permitted to move in one of a first direction and a second direction and prevented from moving in an opposite direction from which the pawl is permitted to move when the pawl engages the third rack.

16. The applier of claim 1 wherein the actuator comprises a trigger, a handle and a pivot link, the trigger having a proximal end, a distal end, and a first pin extending from the proximal end of the trigger, the trigger being rotatably connected to the handle through a second pin and the trigger is connected to the pivot link through the first pin being disposed through a slot on the pivot link, the pivot link being rotatably connected to the handle, the trigger rotating about first axis and the pivot link rotating about a second axis different and offset from the first axis.

17. The applier of claim 16 further comprising a third rack disposed on the pivot link.

18. The applier of claim 17 wherein the trigger and the pivot link are permitted to move in a first direction when a pawl is engaging the third rack and the third rack is moving in the first direction and prevented from moving in a second direction, the second direction being opposite from the first direction.

19. The applier of claim 16 wherein the pivot link is connected to the proximal end of the trigger and is connected to the handle by a third pin extending through a portion in between the distal and proximal end of the trigger and through the second axis, the third pin located between the first and second pins.

20. The applier of claim 16 wherein the pivot link rotatably mounted to the handle defines a first stroke arc having a center along the second axis and the trigger rotatably mounted to the handle defines a second stroke arc having a center along the first axis, the first stroke arc being shorter than the second stroke arc.

21. The applier of claim 16 further comprising a swing cover rotatably mounted to the handle.

22. The applier of claim 21 wherein the swing cover when in an open position exposes portions of a ratchet mechanism and in a close position covers the ratchet mechanism.

23. The applier of claim 1 further comprising a cartridge floor including a finger with an angled portion guiding a clip towards the feeder.

24. The applier of claim 23 wherein the finger has a width smaller than a width of the cartridge floor to further guide a clip towards the feeder.

25. The applier of claim 24 further comprising a bottom housing positioned beneath the cartridge floor and the feeder.

26. The applier of claim 1 wherein the second rack is not connected to a spring.

* * * * *